(12) United States Patent
Albert et al.

(10) Patent No.: US 7,473,761 B2
(45) Date of Patent: Jan. 6, 2009

(54) SOMATOSTATIN ANALOGUES

(75) Inventors: Rainer Albert, Basel (CH); Wilfried Bauer, Lampenberg (CH); David Bodmer, Klingnau (CH); Christian Bruns, Freiburg (DE); Ivo Felner, Reinach (CH); Heribert Hellstern, Heitersheim (DE); Ian Lewis, Riehen (CH); Mark Meisenbach, Durmenach (FR); Gisbert Weckbecker, Biel-Benken (CH); Bernhard Wietfeld, Efringen-Kirchen (DE)

(73) Assignee: Novartis AG, Basel (CH)

( * ) Notice: Subject to any disclaimer, the term of this patent is extended or adjusted under 35 U.S.C. 154(b) by 878 days.

(21) Appl. No.: 10/343,288

(22) PCT Filed: Jul. 30, 2001

(86) PCT No.: PCT/EP01/08824

§ 371 (c)(1),
(2), (4) Date: Aug. 26, 2003

(87) PCT Pub. No.: WO02/10192

PCT Pub. Date: Feb. 7, 2002

(65) Prior Publication Data

US 2005/0014686 A1    Jan. 20, 2005

(51) Int. Cl.
*C07K 7/64*    (2006.01)
(52) U.S. Cl. .................... 530/317; 514/11; 530/311
(58) Field of Classification Search ............. 514/11; 530/317, 311
See application file for complete search history.

(56) References Cited

U.S. PATENT DOCUMENTS 3,863,008 A    1/1975    Grant
4,292,972 A    10/1981    Pawelchak et al.
4,505,897 A    3/1985    Coy et al.
4,612,366 A    9/1986    Nutt .......................... 530/311

FOREIGN PATENT DOCUMENTS

| EP | 029310 | 5/1981 |
|---|---|---|
| EP | 389180 | 9/1990 |
| EP | 395417 | 10/1990 |
| WO | WO 90/12811 | 11/1990 |
| WO | WO 94/00489 | 1/1994 |
| WO | WO 95/00553 | 1/1995 |
| WO | WO 95/03330 | 2/1995 |
| WO | WO 95/04752 | 2/1995 |
| WO | WO 97/01579 | 1/1997 |
| WO | WO 97/05167 | 2/1997 |
| WO | WO 97/43278 | 11/1997 |
| WO | WO 98/04583 | 2/1998 |
| WO | WO 99/65508 | 12/1999 |
| WO | WO 00/12111 | 3/2000 |

OTHER PUBLICATIONS

Huang et al., "Main Chain and Side Chain Chiral Methylated Somatostatin Analogs; Syntheses and Conformational Analyses", *J. Am. Chem. Soc.*, vol. 114, No. 24, pp. 9390-9401 (1992).
Rohrer et al., "Rapid Identification of Subtype-Selective Agonists of the Somatostatin Receptor Trhough Combinatorial Chemistry", *Science*, vol. 282, pp. 737-740 (1998).
Pollak, Polychronakos and Guyda, "Somastostatin Analogue SMS 201-995 Reduces Serum IGF-I Levels in Patients with Neoplasms Potentially Dependent on IGF-I", *Anticancer Res.*, vol. 9, No. 4, pp. 889-892 (1989).
Lloyd-Williams et al., "Convergent Solid-Phase Peptide Synthesis," Tetrahedron, vol. 49, No. 46, pp. 11065-11133 (1993).

*Primary Examiner*—David Lukton
(74) *Attorney, Agent, or Firm*—Gregory C. Houghton

(57) ABSTRACT

The invention provides cyclo[{4-($NH_2$—$C_2H_4$—NH—CO—O—)Pro}-Phg-DTrp-Lys-Tyr(4-Benzyl)-Phe], optionally in protected form, or a pharmaceutically acceptable salt or complex thereof, which has interesting pharmaceutical properties.

8 Claims, No Drawings

SOMATOSTATIN ANALOGUES

This application is a 371 of PCT/EP01/08824 filed Jul. 30, 2001, which claims priority to application GB 0018891.2, filed Aug. 1, 2000.

The present invention relates to somatostatin peptidomimetics, a process for their production and pharmaceutical preparations containing them.

More particularly the present invention provides the compound of formula

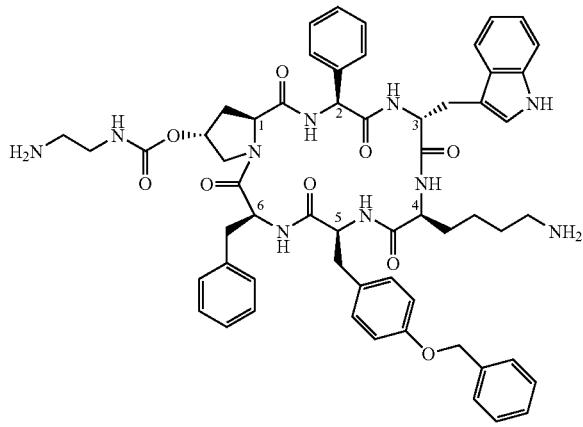

also called cyclo[{4-(NH$_2$—C$_2$H$_4$—NH—CO—O—)Pro}-Phg-DTrp-Lys-Tyr(4-Bzl)-Phe], referred herein to as Compound A, as well as diastereoisomers and mixtures thereof, in free form, in salt or complex form or in protected form. Phg means —HN—CH(C$_6$H$_5$)—CO— and Bzl means benzyl.

Compound A in protected form corresponds to above molecule wherein at least one of the amino groups is protected and which by deprotection leads to Compound A, preferably physiologically removable. Suitable amino protecting groups are e.g. as disclosed in "Protective Groups in Organic Synthesis", T. W. Greene, J. Wiley & Sons NY (1981), 219-287, the contents of which being incorporated herein by reference. Example of such an amino protecting group is acetyl.

When Compound A exists in complex form, it may conveniently be a Compound A bearing a chelating group on the side chain amino group of Pro and complexed with a detectable or radiotherapeutic element. Compound A bearing a chelating group is referred to hereinto as conjugated Compound A.

Examples of chelating groups include e.g. those derived from poly-aminopolycarboxylic acids or anhydrides, e.g. those derived from non cyclic ligands e.g. diethylene triamine pentaacetic acid (DTPA), ethylene glycol-0,0'-bis(2-aminoethyl)-N,N,N',N'-tetraacetic acid (EGTA), N,N'-bis(hydroxybenzyl)ethylenediamine-N,N'-diacetic acid (HBED) and triethylenetetramine hexaacetic acid (TTHA), those derived from substituted DTPA, e.g. p-isothiocyanato-benzyl-DTPA, those derived from macrocyclic ligands, e.g. 1,4,7,10-tetra-azacyclododecane-N,N',N'',N'''-tetraacetic acid (DOTA) and 1,4,8,11-tetraazacyclotetradecane-N,N',N'',N'''-tetraacetic acid (TETA), or 1,4,7,10-tetraazacyclotridecane-N,N',N'',N'''-tetra-acetic acid (TITRA).

The chelating group may be attached either directly or through a spacer to the side chain amino group of Pro. Suitable spacers include those known in the art, e.g. as disclosed in GB-A-2,225,579, for example the divalent residue of an amino-carboxylic acid, for example β-Ala or a divalent residue derived from 6-amino-caproic acid.

Preferred chelating groups are those derived from DTPA, DOTA or TETA. Chelating groups derived from DTPA or DOTA are most preferred.

By detectable element is meant any element, preferably a metal ion which exhibits a property detectable in vivo diagnostic techniques, e.g. a metal ion which emits a detectable radiation or a metal ion which is capable of influencing NMR relaxation properties. By radiotherapeutic element is meant any element which emits a radiation having a beneficial effect on the conditions to be treated.

Suitable elements include for example heavy elements or rare earth ions, e.g. as used in CAT scanning (Computer axial tomography), paramagnetic ions, e.g. $Gd^{3+}$, $Fe^{3+}$, $Mn^{2+}$ and $Cr^{2+}$, fluorescent metal ions, e.g. $Eu^{3+}$, and radionuclides, e.g. a radiolanthanide, particularly a γ-emitting radionuclide, β-emitting radionuclide, α-emitting radionuclide, Auger-e$^-$-emitting radionuclide or a positron-emitting radionuclide e.g. $^{68}$Ga, $^{18}$F or $^{86}$Y.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radioisotopes from Gallium, Indium, Technetium, Ytterbium, Rhenium, Terbium, Lutetium, Thallium and Samarium e.g. $^{67}$Ga, $^{111}$In, $^{99m}$Tc, $^{161}$Tb, $^{169}$Yb, $^{186}$Re or $^{177}$Lu.

Suitable β-emitting radionuclides include those which are useful in radiotherapeutic applications, for example $^{90}$Y, $^{67}$Cu, $^{186}$Re, $^{188}$Re, $^{169}$Er, $^{121}$Sn, $^{127}$Te, $^{177}$Lu, $^{143}$Pr, $^{198}$Au, $^{109}$Pd, $^{165}$Dy, $^{142}$Pr or $^{153}$Sm.

Suitable α-emitting radionuclides are those which are used in therapeutic treatments, e.g. $^{211}$At, $^{212}$Bi or $^{201}$Tl.

Compound A may exist e.g. in free or salt form. Salts include acid addition salts with e.g. inorganic acids, polymeric acids or organic acids, for example with hydrochloric acid, acetic acid, lactic acid, aspartic acid, benzoic acid, succinic acid or pamoic acid. Acid addition salts may exist as mono- or divalent salts, e.g. depending whether 1 or 2 acid equivalents are added to the Compound A in free base form. Preferred salts are the lactate, aspartate, benzoate, succinate and pamoate including mono- and di-salts, more preferably the aspartate di-salt and the pamoate monosalt.

The conjugated Compound A may additionally exist in salt forms obtainable with the carboxylic acid groups when present in the chelating group, e.g. alkali metal salts such as sodium or potassium, or substituted or unsubstituted ammonium salts.

The present invention also includes a process for the production of Compound A. It may be produced in analogy to known methods, for example:

a) cyclising a linear peptide in protected, polymer-bound or unprotected form in such a way that Compound A is obtained and then optionally removing the protecting group(s), b) to produce a conjugated Compound A linking together a chelating group and the Compound A in protected or unprotected form and then optionally removing the protecting group, and recovering Compound A or a conjugated Compound A thus obtained, in free form, in salt form or optionally complexed with a detectable or radiotherapeutic element.

It is generally not critical which amino acid is selected to be at the C-terminal position to start the peptide chain since the linear peptide will be cyclized, provided only that the sequence of amino acids in the linear peptide corresponds to that in Compound A. However there may be other factors which may prefer one starting amino acid over another. When Compound A is prepared by solid phase synthesis, the first amino-acid is preferably attached to the resin, e.g. a commercially available polystyrene-based resin, through a suitable linker, e.g. a linker which is cleavable under mild conditions to keep the side chain protection intact, e.g. SASRIN or an optionally substituted trityl based linker, for example 4-(hydroxy-diphenyl-methyl)-benzoic acid wherein one the phenyl groups may optionally be substituted e.g. by Cl. The building up of the desired peptide chain may be effected in conventionnal manner, e.g. using amino-acid units wherein the terminal amino group is Fmoc-protected, the side chain amino groups where present being protected with a different amino protecting group, e.g. Boc or CBO. Preferably the linear peptide is cyclized in such a way to produce a bond between Tyr(4-Bzl)-OH and Phe, e.g. Phe-{4-(NHR$_1$—CH$_4$—NH—CO—O—)Pro}-Phg-DTrp(R$_2$)-Lys(ε-NHR$_3$)-Tyr(4-Bzl)-OH or a functional derivative thereof, wherein each of R$_1$, R$_2$ and R$_3$ is an amino protecting group. The cyclisation step a) may conveniently be performed according to known method, e.g. via an azide, an active ester, a mixed anhydride or a carbodiimide. Thereafter the protecting groups are removed, e.g. by cleavage e.g. with trifluoroacetic or by hydrogenation.

The cyclisation of the peptide may also be performed directly on the solid support, the first amino acid being in a Nα- and C-terminal protected form and attached through a side chain, e.g. ε-amino function of Lys or by backbone anchoring. The linear sequence is then synthesized following standard solid phase synthesis (SPPS) procedures. After cleavage of the C-terminal protection the peptide is cyclized e.g. as described above. Thereafter the cyclic peptide is cleaved from the resin and deprotected.

If desired, the lateral chain present on Pro may be introduced on the amino acid prior to or after the peptide cyclisation step a). Thus, Pro as a starting amino-acid or a starting linear or cyclic peptide wherein in each case Pro is ring-substituted by OH, may be converted to provide Compound A or the desired Pro unit or the corresponding linear peptide, respectively, wherein Pro is substituted by NHR$_1$—C$_2$H$_4$—NH—CO—O—.

The complexation of a conjugated Compound A may be performed by reacting the conjugated Compound A with a corresponding detectable or radiotherapeutic element yielding compound, e.g. a metal salt, preferably a water-soluble salt. The reaction may be carried out by analogy with known methods, e.g. as disclosed in Perrin, Organic Ligand, Chemical Data Series 22. NY Pergamon Press (1982); in Krejcarit and Tucker, Biophys. Biochem. Res. Com. 77: 581 (1977) and in Wagner and Welch, J. Nucl. Med. 20: 428 (1979).

The following examples are illustrative of the invention. All temperatures are in ° C.

Abbreviations:
ACOH=acetic acid
Boc=tert.-butoxy-carbonyl
Bzl=benzyl
CBO=carbenzoxy
DIPCI=N,N'-diisopropylcarbodiimide
DIPEA=diisopropylethylamine
DMF=dimethylformamide
DPPA=diphenylphosphorylazide
Fmoc=fluorenylmethoxycarbonyl
HOBT=1-hydroxybenzotriazole
Osu=N-hydroxysuccinimide
TFA=trifluoroacetic acid
THF=tetrahydrofuran

EXAMPLE 1

Cyclo[{4-(NH$_2$—C$_2$H$_4$—NH—CO—O—)Pro}-Phg-DTrp-Lys-Tyr(4-Bzl)-Phe]

a) Synthesis of Fmoc-Pro(4-OCO—NH—CH$_2$—CH$_2$—NH-Boc)-OH

L-hydroxyproline methylester hydrochloride is reacted with Fmoc-OSu in aqueous 1.0 N sodium carbonate/THF at room temperature. After completion of the reaction, Fmoc-Pro(4-OH)—OMe is isolated by precipitation. Fmoc-Pro(4-OH)—OMe is then added dropwise into a solution of trisphosgene (0.6 eq.) in THF to give a chlorocarbonate intermediate. After 1 h dimethylaminopyridine (1.0 eq.) and N-Boc-diaminoethane (6.0 eq.) are added and the reaction is stirred at room temperature. After completion of the reaction, the solvent is removed in vacuo and the resulting Fmoc-Pro(4-OCO—NH—CH$_2$—CH$_2$—NH-Boc)-OMe is extracted from a two phase system of ethyl acetate/0.1 M HCl to give crude product (MH$^+$=554) which is purified by crystallization from ethyl acetate. The methyl ester is then cleaved to the free acid by treatment with 1N NaOH in dioxane/water and the product Fmoc-Pro(4-OCO—NH—CH$_2$—CH$_2$—NH-Boc)-OH is purified on silica gel, [(M+Na)]$^+$=562).

b) H-Phe-Pro(4-OCO—NH—CH$_2$—CH$_2$—NH-Boc)-Phg-DTrp(Boc)-Lys(Boc)-Tyr(Bzl)-OH

Commercially available Fmoc-Tyr(Bzl)-O—CH$_2$-Ph(3-OCH$_3$)—O—CH$_2$-Polystyrene resin (SASRIN-resin, 2.4 mM) is used as starting material and carried through a standard protocol consisting of repetitive cycles of Nα-deprotection (Piperidine/DMF, 2:8), repeated washings with DMF and coupling (DIPCI: 4.8 mM/HOBT: 6 mM, DMF). The following amino acid-derivatives are sequentially coupled: Fmoc-Lys(Boc)-OH, Fmoc-DTrp(Boc)-OH, Fmoc-Phg-OH, Fmoc-Pro(4-OCO—NH—CH$_2$—CH$_2$—NH-Boc)-OH, Fmoc-Phe-OH. Couplings (2 eq. amino acids) are continued or repeated until completion, i.e. until complete disappearance of residual amino groups which is monitored by a negative 'Kaiser' Ninhydrin test. Before cleavage of the completely assembled protected linear peptide from its resin support the Nα-Fmoc protection from the last residue is removed.

c) H-Phe-Pro(4-OCO—NH—CH$_2$—CH$_2$—NH-Boc)-Phg-DTrp(Boc)-Lys(Boc)-Tyr(Bzl)-OH

After washings with CH$_2$Cl$_2$, the peptide-resin is transferred into a column or a stirred suction filter and the peptide fragment is cleaved and eluted with a short treatment with 2% TFA in CH$_2$Cl$_2$ within 1 h. The eluate is immediately neutralized with a saturated NaHCO$_3$ solution. The organic solution is separated and evaporated and the side chain protected precursor (MH$^+$=1366) is cyclized without further purification.

d) cyclo[-Pro(4-OCO—NH—CH$_2$—CH$_2$—NH$_2$)-Phg-DTrp-Lys-Tyr(Bzl)-Phe-], trifluoroacetate The above linear fragment is dissolved in DMF (4 mM), cooled to minus 5° C. and treated with 2 eq. DIPEA then 1.5 eq. of DPPA and stirred until completion (ca. 20 h) at 0-4° C. The solvent was almost completely removed in vacuo; the concentrate is diluted with ethyl acetate, washed with NaHCO$_3$, water, dried and evaporated in vacuo.

For deprotection the residue is dissolved at 0° C. in TFA/H$_2$O 95:5 (ca. 50 mM) and stirred in the cold for 30 min. The product is then precipitated with ether containing ca. 10 eq. HCl, filtered, washed with ether and dried. In order to completely decompose remaining Indole-N carbaminic acid the product is dissolved in 5% AcOH and lyophilized after 15 h at ca. 5° C. Preparative RP-HPLC is carried out on a C-18 10 µm STAGROMA column (5-25 cm) using a gradient of 0.5% TFA to 0.5% TFA in 70% acetonitrile. Fractions containing the pure title product are combined, diluted with water and lyophilized. The lyophilisate is dissolved in water followed by precipitation with 10% $Na_2CO_3$ in water. The solid free base is filtered of, washed with water and dried in vacuum at room temperature. The resulting white powder is directly used for the different salts.

EXAMPLE 2

Cyclo[{4-($NH_2$—$C_2H_4$—NH—CO—O-)Pro}-Phg-DTrp-Lys-Tyr(4-Bzl)-Phe] in salt form a. Acetate Conversion to the acetate salt form is carried out using an ion-exchange resin (e.g. AG 3-X4). MS (ESI): m/z 524.5 $[M+2H]^{2+}$ $[\alpha]_D^{20}$=−42°, c=0.26 in AcOH 95% b. Aspartate

Conversion to the mono- or di-aspartate is obtained by reacting 1 equivalent of the compound of Example 1 with 1 or 2 equivalent of aspartic acid in a mixture of acetonitrile/water 1:3. The resulting mixture is frozen and lyophilized. The di-aspartate may also be obtained by dissolving the compound of Example 1 in water/acetonitrile 4:1, filtering, loading on a an ion-exchange resin, e.g. BioRad AG4X4 column, and eluting with water/acetonitrile 4:1. The eluate is concentrated, frozen and lyophilized. $[\alpha]_D^{20}$=−47.5°, c=2.5 mg/ml in methanol c. Benzoate Conversion to the benzoate may be obtained by dissolving the compound of Example 1 with 2 equivalents of benzoic add in a mixture of acetonitrile/Water 1:2. The resulting mixture is frozen and lyophilized.

d. Pamoate 1 equivalent of the compound of Example 1 is dissolved together with 1 equivalent of embonic acid in a mixture of acetonitrile/THF/water 2:2:1. The resulting mixture is frozen and lyophilized.

EXAMPLE 3

Cyclo[{4-(DOTA-NH—$C_2H_4$—NH—CO—O-)Pro}-Phg-DTrp-Lys-Tyr(4-Bzl)-Phe a) cyclo[-Pro(4-OCO—NH—$CH_2$—$CH_2$—$NH_2$)-Phg-DTrp-Lys(Cbo)-Tyr(Bzl)-Phe-], trifluoroacetate The compound is synthesised in the same way like cyclo[-Pro(4-OCO—NH—$CH_2$—$CH_2$—$NH_2$)-Phg-DTrp-Lys(Cbo)-Tyr(Bzl)-Phe-], trifluoroacetate by using Fmoc-Lys(Cbo)-OH instead of Fmoc-Lys(Boc)-OH.

b) 400 mg commercially available DOTAx$2H_2O$ (SYMA-FEX—France) is dissolved in 20 ml water. After addition of 20 ml DMF, 170 mg cyclo[-Pro(4-OCO—NH—$CH_2$—$CH_2$—$NH_2$)-Phg-DTrp-Lys(CBO)-Tyr(Bzl)-Phe-], together with 190 mg DCCl and 60 mg N-hydroxysuccinimide are added. The resulting suspension is kept at room temperature for 72 hours. After filtration, the solvent is removed under reduced pressure and the remaining crude is purified on silica gel (DCM/MeOH/$HOAc_{50\%}$ 8/2/0.25→7/3/1 as mobile phase).

c) For deprotection the above DOTA-conjugate is treated with 5 ml trifluoroacetic acid/thioanisole (9/1) for two hours at room temperature. After that the solution is poured into a mixture of 100 ml diethylether+5 ml 3N HCl/diethylether and the resulting precipitate ias isolated by filtration. Purification is performed on silica gel using DCM/MeOH/$HOAc_{50\%}$ 7/4/2→7/5/4 as mobile phase. Analytically pure endproduct is obtained after a desalting step using a 0.1% TFA to 0.1% TFA in 90% $CH_3CN$ gradient on a $RP_{18}$-HPLC column (Spherisorb 250×4.6 mm). $MH^+$: 1434.7

Compound A in free form or in the form of pharmaceutically acceptable salts and complexes exhibits valuable pharmacological properties as indicated in in vitro and in vivo tests and is therefore indicated for therapy.

More particularly, Compound A exhibits an interesting binding profile for human somatostatin receptors (hsst), particularly with respect to hsst1, hsst2, hsst3 and hsst5. 5 somatostatin receptor subtypes, sst1, sst2, sst3, sst4 and sst5 have been cloned and characterized. hsst1, hsst2 and hsst3 and their sequences have been disclosed by Y. Yamada et al. in Proc. Nat. Acad. Sci., 89, 251-255 (1992). hsst4 and its sequence have been disclosed by L. Rohrer et al. in Proc. Acad. Sci., 90, 4196-4200 (1993). hsst5 and its sequence have been described by R. Panetta et al. in Mol. Pharmacol. 45, 417-427, 1993.

The binding assays may be carried out as disclosed hereunder using membranes from cell lines expressing selectively and stably hsst1, hsst2, hsst3, hsst4 or hsst5, e.g. CHO or COS cells.

Membranes are prepared according to known methods, e.g. as disclosed by C. Bruns et al. in Biochem. J., 1990, 65, page 3944. Membranes prepared from hsst selective cell lines, e.g. CHO or COS cells stably expressing hsst1 or hsst2 or hsst3 or hsst4 or hsst5 are incubated in triplicate in a total volume of 300 µl at 22° C. for 30 min with increasing concentrations of $[^{125}I-Tyr^{11}]$-SRIF-14 in 10 mmol/l Hepes buffer (pH 7.6) containing 0.5% BSA. The incubation is terminated by rapid filtration and the filters are counted in a counter. Specific binding is total binding minus non-specific binding in the presence of 1 µmol/l somatostatin-14. The experiments are carried out in triplicate. The affinity constant ($K_D$) and number of binding sites are calculated using appropriate statistics and graphical programs.

Compound A has in the above binding assays towards hsst1, hsst2, hsst3 and/or hsst5 an $IC_{50}$ in the nMolar range, preferably an $IC_{50}$ of from 0.1 to 10 nM ($IC_{50}$=concentration for half-maximal inhibition in a competition binding assay using $[^{125}I-Tyr^{11}]$-SRIF-14 as hsst1-5 specific radioligand.

| | $IC_{50}$ | | | | |
|---|---|---|---|---|---|
| | hsst1 | hsst2 | hsst3 | hsst4 | hsst5 |
| Compound A | 9.3 nM ± 0.1 | 1.0 nM ± 0.1 | 1.5 nM ± 0.3 | >100 nM | 0.16 nM ± 0.1 |

Compound A also binds to growth hormone secretagogue receptors. Such receptors are disclosed by G. Muccioli et al., J. Endocrinol. 1998, 157, 99-106, by H. Ong et al., in Endocrinology 1998, 139, 432-435 and by R. G. Smith et al., Horm. Res., 1999, 3), 1-8. The binding assay to these receptors may be carried out as disclosed in J. Endocrinol. Invest. 24: RC1 -RC3, 2001. In this assay, Compound A displaces $^{125}$I-Tyr-Ala-hexarelin. Compound A is accordingly useful for modulating the activity of growth hormone secretagogue receptors, e.g. indicating a possible role in body weight gain or metabolic regulation.

Furthermore, Compound A shows GH-release inhibiting activity as indicated by the inhibition of GH release in vitro from cultured pituitary cells. For example, anterior pituitary glands from adult male rats are cut into small pieces and dispersed using 0.1% trypsin in 20 mM HEPES buffer. The dispersed cells are cultured for four days in MEM (Gibco) supplemented with 5% fetal calf serum, 5% horse serum, 1 mM NaHCO$_3$, 2.5 nM dexamethasone, 2.5 mg/ml insulin and 20 U/ml Pen/Strep. On the day of the experiment the attached cells are washed two times with Krebs-Ringer medium buffered with 20 mM HEPES and supplemented with 5 mM glucose and 0.2% BSA. Subsequently the cells are incubated for three hours with Compound A in the presence of $3\times10^{-10}$ M growth hormone releasing factor. The amount of growth hormone released into the medium is measured by RIA. Compound A has an IC$_{50}$ of 0.4 nM in this assay.

Compound A inhibits the release of growth hormone (GH) in rats. Compound A is administered s.c. to anaesthetized rats. Blood is collected after decapitation 1 h after administration of the compound. The duration of action is estimated on the basis of the inhibition of basal GH secretion 6 h after drug treatment. Hormone levels are measured by RIA 1 h and 6 h after treatment. The ID$_{50}$-value for the inhibition of the hormone secretion is determined graphically (log-probit) for each experiment and the resulting values are averaged logarithmically. In this in vivo model Compound A significantly inhibits growth hormone release with a long duration of action (Mean basal ID$_{50}$=5.5 µg/kg s.c. 6 h). In a similar assay for measuring the effect on insulin, Compound A inhibits insulin secretion.

The potent and efficacious inhibition of GH was also confirmed in monkey studies. Moreover, metabolic studies in diabetic monkeys demonstrated a potent antidiabetic/insulin-sensitizing effect of Compound A.

Furthermore, Compound A inhibits IGF-1 plasma levels in vivo as indicated in standard tests using male rats. Briefly, Compound A is administered by osmotic pump implanted s.c. to male rats of a L wis strain. Blood samples are collected from the retrobulbar plexus using a short anesthesia with e.g. isoflurane. In this assay, Compound A significantly lowers IGF-1 plasma levels with a long lasting effect: e.g. more than 60% inhibition is observed after 14 days of treatment with 10 µg/kg/h of Compound A. More particularly no escape could be observed after continuous treatment in rat recipients of aorta or kidney allografts continuously infused with Compound A at 10 µg/kg/h up to 126 days which induces a significant and persistent lowering of IGF-1 plasma levels.

Compound A is accordingly useful for the prevention or treatment of disorders with an aetiology comprising or associated with excess GH-secretion and/or excess of IGF-1 e.g. in the treatment of acromegaly as well as in the treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity. Compound A is also useful in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g variceal oesophagial bleeding.

Compound A is also useful in the treatment of tumors which are somatostatin receptor positive, e.g. tumors bearing hsst1, hsst2, hsst3 and/or hsst5, as indicated in proliferation tests with various cancer cell lines bearing such somatostatin receptors.

The AR42J rat pancreatic tumor cell line is derived from an azaserine-induced exocrine pancreatic tumor (Jessop and Hay, 1980). Mycoplasma cell-free cultures are propagated in DMEM supplemented with 10% fetal calf serum (FCS) at 5% CO$_2$. Cells are grown in the absence of antibiotics or antifungal agents. Subconfluent AR42J cells are trypsinized, diluted in DMEM+2.5% FCS and seeded in uncoated 96-well plates. After a 48-hr incubation period (Day O), the number of cells in a separate control plate Is determined both by counting cells in a Coulter counter and by the SRB calorimetric assay. The cells are then exposed to Compound A for 2 to 5 days at various concentrations and then counted. Under these conditions Compound A inhibits the proliferation of the tumor cells at concentrations ranging from $10^{-12}$ to $10^{-6}$ M.

Tumor Growth Studies in vivo

Female nude mice weighing 19-22 g are kept in groups of 5 animals and have free access to drinking water and a pathogen-free rodent diet. Subcutaneous tumors are initiated from cultured AR42J cells. Treatment commences 2-4 days following inoculation of the tumor cells, Compound A is administered as a continuous infusion, e.g. at a rate of 10 to 50 µg/kg/hr. The size of the tumors is determined with a caliper. For statistical calculations Student's t-test is applied. In this assay Compound A inhibits tumor growth at day 11 by 51% vs saline control.

Compound A is thus useful for the treatment of malignant cell proliferative diseases, e.g. cancer tumors, particularly tumors bearing the somatostatin receptor types to which it has a binding affinity, e.g. as disclosed hereunder for the complexed conjugated Compound A.

Compound A also has an inhibiting effect on angiogenesis, as indicated in standard tests, e.g. in nude mice. Briefly, tumor cells (0.1 to $10\times10^6$ in 0.1 ml) (SiHa cells and MDA MB-231 cells prepared as disclosed in Angiogenesis, Ed. by R. Steiner, P. B. Weisz and R. Langer, 1992, Switzerland) are inoculated intracutaneously. Usually two midventral sites/mouse are injected which are located distant from the main ventral skin vessels so that the background vessel count is low. Control groups receive 0.1 ml 0.02% trypan blue in PBS. 10 days following injection, anesthetized mice are sacrificed by CO$_2$ inhalation. The skin is mounted onto a plastic ring (40 mm diameter) for evaluation by an inverted microscope (Zeiss IM) at 12.5- and 25-fold magnification. As a measure of angiogenesis, vessels are photographed and those are counted that are directly connected with the tumor. In control animals those vessels are counted that are connected to a defined area around the injection site. This area corresponds to the mean area of the dermal tumors. The latter is determined by use of a caliper according to the equation $3.14 \times r^2$. Compound A is administered s.c. either on the day of tumor inoculation or 3 days later. Control animals are vehicle-treated. In this assay, Compound A inhibits blood vessel formation when administered at a dose of e.g. 0.01 to 1000 µg/kg s.c.

Compound A is thus useful for the prevention or treatment of angiogenesis, inflammatory disorders as indicated above including inflammatory eye diseases, macular edema, e.g. cystoid macular edema, idiopathic cystoid macular edema, exudative age-related macular degeneration, choroidal neovascularization related disorders and proliferative retinopathy.

Compound A also has an inhibiting effect on the proliferation and migration of smooth muscle cells as indicated in following tests.

Chronic Allograft Rejection

The kidney of a male DA ($RT1^a$) rat is orthotopically transplanted into a male Lewis ($RT1^1$) recipient. In total 24 animals are transplanted. All animals are treated with cyclosporine A at 7.5 mg/kg/day per os for 14 days starting on the day of transplantation, to prevent acute cellular rejection. Contralateral nephrectomy is not performed. Each experimental group treated with a distinct dose of Compound A or placebo comprises six animals. Starting 14 days after transplantation, the recipient animals are treated up to 112 days by infusion with Compound A or receive placebo. At 14 days after transplantation organ perfusion is measured by MRI. This is repeated at days 53-64 after transplantation and at the end of the experiment. The animals are then autopsied. Administration of Compound A at a dose of 10 µg/kg/h in this rat kidney allograft model results in an improved organ perfusion as well as a reduction in chronic rejection related vascular remodelling and graft infiltration (cellular rejection). A marked and persistent drop of IGF-1 levels has also been measured. These results have been confirmed in a second set of experiments using a heterotopic mouse heart allotransplantation model, demonstrating beneficial effects on vascular remodelling as well as in graft infiltration.

Compound A has also been tested in a carotid artery loop transplantation model using B10.A (2R) ($H-2h^2$) mice as donor and B10.BR ($H-2^k$) mice as recipient. In brief, the donor carotid artery is transplanted paratopically as a loop into the recipients carotid artery by an end-to-side anastomosis. A mini-pump is placed s.c. immediately after transplantation that delivers Compound A at a rate of 50 µg/kg/h. Carotid artery grafts are harvested at 30 days after transplantation to analyse vascular remodeling e.g. by morphometric analysis of Verhoeff elastin stained paraffin sections using a computer-assisted system. In this model Compound A inhibits neointimal formation compared with non-treated animals where a massive neointima is formed.

Angioplasty

Studies on angioplasty are done in the rat model of balloon catheter injury. Balloon catheterization is performed on day 0, essentially as described by Powell et al. (1989). Under Isofluorane anaesthesia, a Fogarty 2F catheter is introduced into the left common carotid artery to obtain a uniform de-endothelialization. The catheter is then removed, a ligature placed around the external carotid to prevent bleeding and the animals allowed to recover. 2 groups of 12 RoRo rats (400 g, approximately 24 weeks old) are used for the study: one control group and one group receiving Compound A and the rats are fully randomized. Compound A is administered by continuous infusion using minipumps at a rate of 10 µg/kg/h starting 2 days before balloon injury (day-3) until the end of the study, 14 days after balloon injury. The rats are then anaesthetized with Isofluorane and perfused with 0.1 M phosphate buffered saline solution (PBS, pH 7.4) and then for 15 min. with 2.5% glutaraldehyde in phosphate buffer (pH 7.4).

Carotid arteries are then excised, separated from surrounding tissue and immersed in 0.1 M cacodylate buffer (pH 7.4) containing 7% saccharose and incubated overnight at 4° C. The following day the carotids are then embedded in Technovit 7100 according to the manufacturers recommendation. The cross-sectional area of the media, neointima and the lumen are evaluated morphometrically by means of an image analysis system (MCID, Toronto, Canada). In this assay, Compound A inhibits neointimal thickening significantly.

Compound A is thus also useful for preventing or combating graft vessel diseases, e.g. allo- or xenotransplant vasculopathies, e.g. graft vessel atherosclerosis, e.g. in a transplant of organ, e.g. heart, lung, combined heart-lung, liver, kidney or pancreatic transplants, or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium.

Compound A has a beneficial plasma half-life. It has an elimination half-life between 15 and 30 hours.

For all the above indications the required dosage will of course vary depending upon, for example, the host, the mode of administration and the severity of the condition to be treated. In general, however, satisfactory results are obtained by administration in the order of from 1 µg to 0.7 mg/kg/day of Compound A. An indicated daily dosage for patients is in the range from about 2 µg to about 50 mg, preferably about 0.01 to about 40 mg, e.g. about 0.01 to about 3 mg s.c. of the compound conveniently administered in divided doses up to 3 times a day in unit dosage form containing for example from about 0.5 µg to about 25 mg, e.g. from about 2 µg to 20 mg, for example from 2 µg to 1.5 mg of the Compound A.

Compound A may be administered in free form or in pharmaceutically acceptable salt form or complexes. Such salts and complexes may be prepared in conventional manner and exhibit the same order of activity as the free compound. The present invention also provides a pharmaceutical composition comprising Compound A in free base form or in pharmaceutically acceptable salt form or complex form, together with one or more pharmaceutically acceptable diluent or carrier. Such compositions may be formulated in conventional manner. Compound A may also be administered in sustained release form, e.g. in the form of implants, microcapsules, microspheres or nanospheres comprising e.g. a biodegradable polymer or copolymer, in the form of a liposomal formulation, or in the form of an autogel, e.g. a solid or semi-solid composition capable of forming a gel after interaction with patient's body fluids.

Compound A or a pharmaceutically acceptable salt or complex thereof may be administered by any conventional route, for example parenterally e.g. in form of injectable solutions or suspensions (including e.g. the sustained release form as indicated above), orally using a conventional absorption enhancer, in a nasal or a suppository form or topically, e.g. in the form of an ophthalmic liquid, gel, oinment or suspension preparation, e.g a liposomal, microsphere or nanosphere formulation, e.g. for instillation or subconjunctival or intra- or peri-ocular injections.

In accordance with the foregoing the present invention further provides:

1. Compound A or a pharmaceutically acceptable salt or complex thereof for use as a pharmaceutical;
2. A method of preventing or treating diseases or disorders as indicated above in a subject in need of such treatment, which method comprises administering to said subject an effective amount of Compound A or a pharmaceutically acceptable salt or complex thereof; or 3. Compound A or a pharmaceutically acceptable salt or complex thereof for use in the preparation of a pharmaceutical composition for use in any method as defined under 2. above.

The conjugated Compound A or a pharmaceutically acceptable salt thereof is useful either as an imaging agent, e.g. visualisation of somatostatin receptor positive tissues and cells e.g. somatostatin receptor positive tumors and metastases, inflammatory or autoimmune disorders exhibiting somatostatin receptors, tuberculosis or organ rejection after transplantation, when complexed with a detectable element, e.g. a γ- or positron-emitting nuclide, a fluorescent metal ion or a paramagnetic ion, e.g. $^{111}$In, $^{161}$Tb, $^{177}$Lu, $^{86}$Y, $^{68}$Ga Eu$^{3+}$, Gd$^{3+}$, Fe$^{3+}$, Mn$^{2+}$ or Cr$^{2+}$, or as a radiopharmaceutical for the treatment in vivo of somatostatin receptor positive tumors and metastases, rheumatoid arthritis and severe inflammation conditions when complexed with an α- or β-emitting nuclide or a nuclide with Auger-e$^-$-cascades, e.g. $^{90}$Y, $^{161}$Tb, $^{177}$Lu, $^{211}$At, $^{213}$Bi or 201Tl, as indicated by standard tests.

In particular, it is observed that the conjugated Compound A binds to somatostatin receptors with pKi values of from about 8 to 10. Compound of Example 3 complexed with e.g. $^{111}$In, $^{88}$Y, $^{90}$Y or $^{177}$Lu binds in the nM range to the respective sst sub-types in accordance with the binding profile of Compound A.

The affinity of the conjugated Compound A and its complexes for somatostatin receptors can also be shown by in vivo testing, according to standard test methods, e.g. as disclosed in GB-A-2,225,579. For example the compound of Example 3 complexed with e.g. $^{111}$In, $^{88}$Y, $^{90}$Y or $^{177}$Lu, gives a significant tumor accumulation 4 hours after injection into mice or rats bearing an exocrine pancreatic tumor expressing hsst2 receptors.

After administration of a conjugated Compound A in complexed form, e.g. a $^{111}$In, $^{177}$Lu, $^{86}$Y or $^{161}$Tb complexed Compound A, at a dosage of from 1 to 5 μg/kg labelled with 0.1 to 5 mCi radionuclide, preferably 0.1 to 2 mCi the tumor site becomes detectable.

The conjugated Compound A when radiolabelled with an α- or β-emitting radionuclide or a nuclide with Auger-e$^-$-cascades exhibits an antiproliferative and/or cytotoxic effect on tumor cells bearing somatostatin receptors, e.g. as indicated in nude mice tests.

Nude mice are inoculated with AR42J rat pancreatic tumor cells or NCI-H69 human small cell lung cancer cells as disclosed above. When tumors have reached a volume of 1 to 2 cm$^3$ animals are randomized into control and treatment groups. Conjugated Compound A in complexed form is administered by i.p. or i.v. injections. Doses up to 40 mCi/kg are given per mouse. The size of the tumors is determined with a caliper as disclosed above. For statistical calculations Student's t-test is applied. In this test, transient tumor shrinkage up to 50% of initial is observed after one week and tumor growth is delayed for two weeks upon a single application of the compound of Example 3 complexed with $^{90}$Y. In contrast the control groups showed continuous tumor growth with a volume doubling time of about seven days.

Accordingly, in a series of specific or alternative embodiments, the present invention also provides:

4. Use of a conjugated Compound A complexed with a detectable element for in vivo detection of somatostatin receptor positive cells and tissues, e.g. somatostatin receptor positive tumors and metastasis, in a subject and recording the localisation of the receptors targeted by said complex;

5. A method for in vivo detection of somatostatin receptor positive tissues and cells, e.g. somatostatin receptor positive tumors and metastasis, in a subject comprising administering to said subject a conjugated Compound A complexed with a detectable element, or a pharmaceutically acceptable salt form, and recording the localization of the receptors targeted by said complex.

The conjugated Compound A in complexed form for use as an imaging agent may be administered e.g. intravenously, e.g. in the form of injectable solutions or suspensions, preferably in the form of a single injection. The radiolabelling may preferably be performed shortly before administration to a subject.

In animals an indicated dosage range may be from 0.01 to 1 μg/kg of a conjugated Compound A complexed with 0.02 to 0.5 mCi γ-emitting radionuclide. In larger mammals, for example humans, an indicated dosage range may be from 1 to 100 μg/m$^2$ conjugated Compound A complexed e.g. with 1 to 100 mCi/m$^2$ detectable element, e.g. $^{111}$In, $^{86}$Y or $^{177}$Lu.

6. Use of a conjugated Compound A complexed with an α- or β-emitting nuclide or a nuclide with Auger-e$^-$-cascades, for in vivo treatment of somatostatin receptor positive tumors and metastases.

7. A method for in vivo treatment of somatostatin positive tumors and metastases, e.g. for treating invasiveness of such tumors or symptoms associated with such tumor growth, in a subject in need of such treatment which comprises administering to said subject a therapeutically effective amount of a conjugated Compound A complexed with an α- or β-emitting nuclide or a nuclide with Auger-e$^-$ cascades.

8. Use of a conjugated Compound A or a pharmaceutically acceptable salt thereof in the manufacture of an imaging agent or a radiopharmaceutical composition.

Dosages employed in practising the radiotherapeutic use of the present invention will of course vary depending e.g. on the particular condition to be treated, for example the known radiotoxicity to normal organs expressing somatostatin receptors, the volume of the tumor and the therapy desired. In general, the dose is calculated on the basis of pharmacokinetik and radioactivity distribution data obtained in to healthy organs and based on the observed target uptake. A β-emitting complex of a conjugated Compound A may be administered repeatedly e.g. over a period of 1 to 3 months.

In animals an indicated dosage range may be from 20 to 100 μg/kg conjugated Compound A complexed with 15 to 70 mCi of an α- or β-emitting nuclide or a nuclide with Auger-e$^-$ cascades, e.g. $^{90}$Y, $^{177}$Lu or $^{161}$Tb. In larger mammals, for example humans, an indicated dosage range may be from 1 to 100 μg/m$^2$ conjugated Compound A complexed e.g. with 1 to 100 mCi/m$^2$ of an α- or β-emitting nuclide or a nuclide with Auger-e$^-$-cascades, e.g. $^{90}$Y, $^{177}$Lu or $^{161}$Tb.

The conjugated Compound A in complexed form for use as a radiotherapeutic agent may be administered by any conventional route, e.g. intravenously, e.g. in the form of injectable solutions. It may also be administered advantageously by infusion, e.g. an infusion over 15 to 60 min. Depending on the site of the tumor, it may be administered as close as possible to the tumor site, e.g. by means of a catheter. The present invention also provides a pharmaceutical composition comprising a conjugated Compound A in free base form or in pharmaceutically acceptable salt form or complexed with a detectable or radiotherapeutic agent, together with one or more pharmaceutically acceptable diluent or carrier.

Compound A or the conjugated Compound A in complexed form may be suitable for imaging or treating somatostatin receptor expressing or accumulating tumors such as pituitary, gastro-enteropancreatic, carcinoids, central nervous system, breast, prostatic (including advanced hormone-refractory prostate cancer), ovarian or colonic tumours, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof, as well as autoimmune or inflammatory disorders, e.g. rheumatoid arthritis, Graves disease or other inflammatory eye diseases.

According to a further aspect of the invention, there is provided a pharmaceutical composition comprising a conjugated Compound A or a complex thereof together with one or more pharmaceutically acceptable carriers or diluents therefor. Such compositions may be manufactured in conventional manner and may be presented, e.g. for imaging, in form of a kit comprising two separate dosages, one being the radionuclide and the other the conjugated Compound A, with instructions for mixing them. For radiotherapy, the conjugated Compound A in complexed form may preferably be in the form of a hot liquid formulation.

Compound A or a conjugated Compound A in complexed form may be administered as the sole active ingredient or in conjuction with, e.g. as an adjuvant to, other drugs. For example, Compound A may be used in combination with an immunosuppressive agent, e.g. a calcineurin inhibitor, e.g. cyclosporin A or FK 506; a macrocyclic lactone having immunosuppressive properties, e.g. rapamycin or 40-O-(2-hydroxyethyl)-rapamycin (RAD); an ascomycin having immunosuppressive properties, e.g. ABT-281, ASM981, etc.; corticosteroids; cyclophosphamide; azathioprene; methotrexate; leflunomide; mizoribine; mycophenolic acid or a salt thereof, e.g. Myfortic®; mycophenolate mofetil; 15-deoxyspergualine or an immunosuppressive homologue, analogue or derivative thereof; an accelerating lymphocyte homing agent, e.g. FTY720; immunosuppressive monoclonal antibodies, e.g., monoclonal antibodies to leukocyte receptors, e.g., MHC, CD2, CD3, CD4, CD7, CD8, CD25, CD28, CD40, CD45, CD58, CD80, CD86 or to their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or 3 antagonists, VCAM-4 antagonists or VLA-4 antagonists. Compound A may also be used in combination with an anti-inflammatory agent, a GH secretagogue receptor modulating agent, e.g. ghrelin or hexarelin, a GH receptor antagonist, e.g. pegvisomant, an insulin secretagogue or insulin secretion enhancer, e.g. a sulphonyl urea, e.g. tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcydamide, a short acting nonsulphonyl urea, an oral insulinotropic agent derivative, e.g. a short acting insulin enhancer, e.g. meglitinide, repaglinide, a phenyl acetic add derivative, e.g. nateglinide, a DPP IV inhibitor, e.g. 1-{2-[(5-cyanopyridin-2-yl)amino] ethylamino}acetyl-(2S)-cyano-pyrrolidine dihydrochloride, LAF237, GLP-1 or a GLP-1 agonist analog, an insulin senzitizer, e.g. a peroxisome proliterator activated receptor γ agonist (PPARγ), e.g. a glitazone, e.g. (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2, 4-dione (darglitazone), 5-{[4-(1-methyl-cyclohexyl) methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)-methyl] phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropane-carbonylamino) benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl) benzoxazol-5-yl]-methyl}thiazolidine-2,4-dione (T-174) or 5-(2,4-dioxothiazolidin-5-ylmethyl)-2-methoxy-N-(4-trifluoromethyl-benzyl)benzamide (KRP297), a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or NN-622, a refinoid X receptor agonist or a rexinoid, e.g. 2-[1-(3,5,5,8, 8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, a protein tyrosine phosphatase kinase 1B, a glucogen synthase kinase-3 inhibitor, a non-peptidyl small molecule insulin mimetic compound, e.g. L-783,281 or CLX-901, or a low dose of insulin, a glutamine: fructosephosphate amidotransferase inhibitor, a glucose-6-phosphatase inhibitor, a biguanide, e.g. Metformin, a fructose-1,6-biphosphatase inhibitor, a glycogen phosphorylase inhibitor, e.g. CP-91149, a glucagon receptor antagonist, e.g. CP-99711, NNC 92-1687, L-168,049 or BAY27-9955, a phosphoenolpyruvate carboxykinase, a pyruvate dehydrogenase kinase inhibitor, an α-Glucosidase inhibitor, e.g. 4",6"-dideoxy-4"-[(1S)-(1,4,6/5)-4,5,6-trihydroxy-3-hydroxymethyl-2-cyclo-hexenylamino)maltotriose or O-4,6-dideoxy-4-{[1S,4R,5S,6S]-4,5,6-trihydroxy-3-(hydroxymethyl)-2-cyclohexen-1-yl]-amino}-α-D-glucopyranosyl-(1→4)-O-α-D-glucopyranosyl-(1→4)-D-glucopyranose (acarbose), N-(1,3-dihydroxy-2-propyl)valiolamine (voglibose) or miglitol, or a gastric emptying inhibitor, e.g. GLP-1, CCK8 and amylin (e.g. Pramlintide), an agent having anti-angiogenetic effects, e.g a benzoporphyrin, e.g. verteporfin, midostaurin or a 4-pyridylmethyl-phtalazine.

Compound A or a conjugated Compound A in complexed form may also be used in combination with an antiproliferative agent, e.g a chemotherapeutic drug, e.g. paclitaxel, gemcitabine, cisplatinum, doxorubicin, 5-fluorouracil or taxol, a hormonal agent or antagonist, e.g. an anti-androgen or mitoxantrone (especially in the case of prostate cancer), or an antiestrogen, like letrozole (especially in the case of breast cancer), an antimetabolite, a plant alkaloid, a biological response modifier, preferably a lymphokine or interferons, an inhibitor of protein tyrosine kinase and/or serine/threonine kinase, or an agent with other or unknown mechanism of action, e.g. any epothilone or epothilone derivative, or a macrocyclic lactone, e.g. rapamycin, RAD or CCI779.

Where Compound A or a conjugated Compound A in complexed form is administered in conjunction with another drug, dosages of the co-administered drug will of course vary depending on the type of co-drug employed, on the specific drug employed, on the condition to be treated, and so forth. The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

In accordance with the foregoing the present invention provides in a yet further aspect:

9. A pharmaceutical combination comprising a) a first agent which is Compound A or a conjugated Compound A in complexed form and b) a co-agent, e.g. as defined above.

10. A method as defined above comprising co-administration, e.g. concomitantly or in sequence, of a therapeutically effective amount of Compound A or a conjugated Compound A in complexed form, and a second drug substance, said second drug substance being, e.g. as indicated above.

The particular combination of the invention will be selected depending on the prevention or treatement of diseases or disorders; e.g. a combination with an immunosuppressive agent for e.g. the prevention or treatement of chronic graft rejection, a combination with an insulin secretagogue, insulin secretion enhancer, insulin sensitizer or a low dose of insulin in the treatment of diabetes or complications thereof, a combination with an anti-inflammatory agent for the prevention or treatment of inflammatory diseases or disorders, a combination with an agent having anti-angiogenetic effects for the prevention or treatment of e.g. macular edema or degeneration or in cancer, a combination with a chemotherapeutic agent for use in cancer.

The invention claimed is:

1. A compound of formula

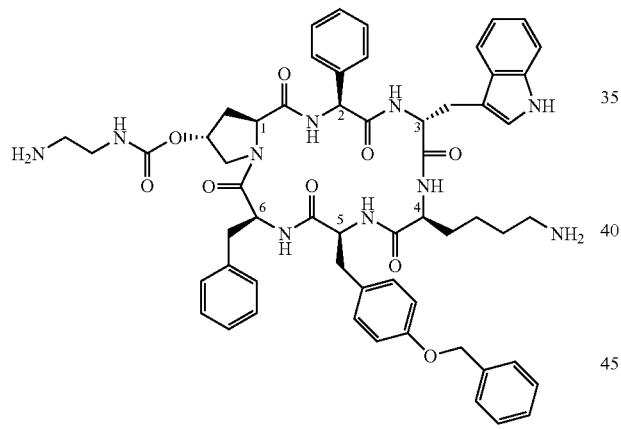

where one of the amino groups being optionally in protected form, or a salt or complex thereof.

2. A compound according to claim 1 in unprotected form, in salt form.

3. A compound according to claim 2 as a mono- or disalt.

4. A compound according to claim 3 in the form of an acetate, benzoate, aspartate or pamoate salt.

5. A pharmaceutical composition comprising a compound according to claim 1 or a pharmaceutically acceptable salt thereof, in association with one or more pharmaceutically acceptable diluent(s) or carrier(s) therefor.

6. A pharmaceutical composition according to claim 5, in a sustained release form or in a topical form.

7. A pharmaceutical composition according to claim 5, for use in combination with an immunosuppressive agent, an anti-inflammatory agent, a GH secretagogue receptor modulating agent, a GH receptor antagonist, an insulin secretagogue, an insulin secretion enhancer, an insulin sensitizer, a low dose of insulin, an agent having anti-angiogenetic effects or a chemotherapeutic agent.

8. A compound of formula

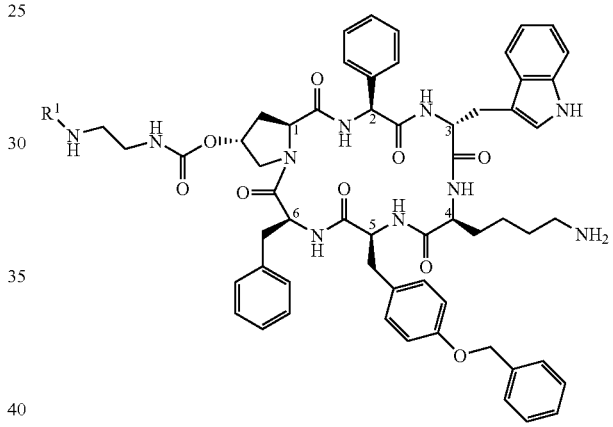

where one of the amino groups being optionally in protected form, or a salt or complex thereof and $R^1$ is a chelating agent, optionally complexed with a detectable or a radiotherapeutic element.

* * * * *

UNITED STATES PATENT AND TRADEMARK OFFICE
CERTIFICATE OF CORRECTION

| | |
|---|---|
| PATENT NO. | : 7,473,761 B2 |
| APPLICATION NO. | : 10/343288 |
| DATED | : January 6, 2009 |
| INVENTOR(S) | : Albert et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1460 days.

Signed and Sealed this
Seventh Day of August, 2012

David J. Kappos
*Director of the United States Patent and Trademark Office*